US00PP27832P2

(12) United States Plant Patent
Hansen

(10) Patent No.: US PP27,832 P2
(45) Date of Patent: Apr. 4, 2017

(54) ***BUDDLEIA* PLANT NAMED 'GLASS SLIPPERS'**

(50) Latin Name: ***Buddleia* hybrid (L.)**
Varietal Denomination: Glass Slippers

(71) Applicant: Hans A. Hansen, Zeeland, MI (US)

(72) Inventor: Hans A. Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 141 days.

(21) Appl. No.: 14/545,725

(22) Filed: Jun. 10, 2015

(51) Int. Cl.
*A01H 5/00* (2006.01)

(52) U.S. Cl.
USPC ..... Plt./242

(58) Field of Classification Search
USPC ..... Plt./226, 242
See application file for complete search history.

(56) References Cited

U.S. PATENT DOCUMENTS

| | | | |
|---|---|---|---|
| PP12,383 | P2 | 2/2002 | Dransfield |
| PP14,370 | P2 | 12/2003 | Turrell |
| PP17,332 | P2 | 1/2007 | Moore |
| PP19,934 | P2 | 4/2009 | Davis |
| PP19,935 | P2 | 4/2009 | Bloom |
| PP19,950 | P3 | 4/2009 | Werner |
| PP19,991 | P3 | 5/2009 | Werner |
| PP22,063 | P2 | 8/2011 | Valin |
| PP22,064 | P2 | 8/2011 | Valin |
| PP22,065 | P2 | 8/2011 | Podaras |
| PP22,066 | P2 | 8/2011 | Podaras |
| PP22,067 | P2 | 8/2011 | Podaras |
| PP22,068 | P2 | 8/2011 | Podaras |
| PP22,069 | P2 | 8/2011 | Podaras |
| PP22,080 | P2 | 8/2011 | Podaras |
| PP22,081 | P2 | 8/2011 | Podaras |
| PP22,098 | P2 | 8/2011 | Podaras |
| PP22,108 | P2 | 9/2011 | Podaras |
| PP22,109 | P2 | 9/2011 | Podaras |
| PP22,110 | P2 | 9/2011 | Podaras |
| PP22,142 | P2 | 9/2011 | Podaras |
| PP22,143 | P2 | 9/2011 | Podaras |
| PP22,144 | P2 | 9/2011 | Podaras |
| PP22,177 | P2 | 10/2011 | Podaras |
| PP22,367 | P2 | 12/2011 | Podaras |
| PP22,465 | P2 | 1/2012 | Brand |
| PP22,680 | P2 | 4/2012 | Senior |
| PP23,214 | P2 | 11/2012 | Moore |
| PP23,425 | P2 | 2/2013 | Brand |
| PP23,461 | P2 | 3/2013 | Valin |
| PP23,462 | P2 | 3/2013 | Valin |
| PP23,463 | P2 | 3/2013 | Valin |
| PP23,464 | P2 | 3/2013 | Valin |
| PP23,498 | P2 | 3/2013 | Podaras |
| PP24,015 | P3 | 11/2013 | Werner |
| PP24,016 | P3 | 11/2013 | Werner |
| PP24,030 | P3 | 11/2013 | Podaras |

*Primary Examiner* — Susan McCormick Ewoldt
*Assistant Examiner* — Karen Redden

(57) ABSTRACT

*Buddleia* 'Glass Slipper' is a short, mounded, multi-stemmed, winter-hardy butterfly bush plant with long, compact, self-cleaning flowering thyrse over a long season beginning mid-summer with sweetly-fragrant pale periwinkle flowers that are attractively offset by silvery green foliage.

1 Drawing Sheet

Botanical classification: *Buddleia* hybrid (L.)
Variety denomination: 'Glass Slippers'.

BACKGROUND AND ORIGIN OF THE PLANT

The present invention relates to the new and distinct winter-hardy butterfly bush plant, *Buddleia* 'Glass Slippers' as a single seedling among thousands of seeds collected by the inventor in the summer of 2011 at a wholesale perennial nursery in Zeeland, Mich., USA. The new plant, originally labeled with the breeder code H11-20-03, is from an open pollination of an unreleased proprietary hybrid *Buddleia* named HK10-212-01 (not patented) as the female or seed parent. The male parent is unknown.

*Buddleia* 'Glass Slippers' was first asexually propagated in 2012 by stem cuttings at the same nursery in Zeeland, Mich. The resultant asexually propagated plants have been found to be stable and true to type in successive generations of asexual reproduction.

*Buddleia* 'Glass Slippers' has not been made publically available nor sold more than a year prior to the filing of this application. All disclosures have either been obtained directly or indirectly from the inventor.

BRIEF SUMMARY OF THE PLANT

*Buddleia* 'Glass Slippers' differs from its parents as well as all other winter-hardy butterfly bush plants known to the applicant in many traits. The foliage color of 'Glass Slippers' is silvery green with icy, light periwinkle blue flowers. The leaf size of 'Glass Slippers' is variable, depending on the position on the stem. Largest leaves are lower on the stem and decrease in size distally. Compared to the proprietary female parent, HK10-212-01, 'Glass Slippers' is more compact in habit and has lighter colored flowers.

The nearest comparison plants include: *Buddleia* 'Podaras #8' U.S. Plant Pat. No. 22,069 (more commonly known as 'Butterfly Heaven'), 'Blue Heaven' U.S. Plant Pat. No. 19,935, 'Lilac Chip' U.S. Plant Pat. No. 24,016, 'Blue Chip' U.S. Plant Pat. No. 19,991 and 'Blue Chip Jr' U.S. Plant Pat. No. 26,581. The flowers of 'Glass Slippers' are lighter than any of the comparison varieties and do not produce anthers.

The habit of 'Glass Slippers' is more mounded than 'Blue Chip' and 'Blue Heaven', and it is taller than 'Blue Chip Jr' and 'Podaras #8' and shorter than 'Blue Chip', 'Butterfly Heaven' and 'Lilac Chip'.

The following Table 1 further demonstrates some comparisons with the new plant and the nearest comparison cultivars at three-years old.

TABLE 1

| CULTIVAR | Leaf color | Flower color | Habit | Size (H × W) |
|---|---|---|---|---|
| 'Blue Chip' | green | blue | upright | 110 cm × 100 cm |
| 'Blue Chip Jr' | green | blue-purple | low mound | 80 cm × 125 cm |
| 'Butterfly Heaven' | green | lilac-purple | upright | 180 cm × 120 cm |
| 'Glass Slippers' | silvery green | pale periwinkle | mounded | 135 cm × 150 cm |
| 'Lilac Chip' | green | purplish-pink | broad mound | 80 cm × 125 cm |
| 'Podaras #8' | light green | lavender | mounded | 90 cm × 95 cm |

*Buddleia* 'Glass Slippers' is a unique winter-hardy butterfly bush different from all other *Buddleia* cultivars known to the inventor based on the following combined traits:

1. Winter-hardy shrub, with multiple-stemmed, branched, short, mounded habit.
2. Many-flowered compact thyrse over a prolonged season beginning mid-summer.
3. Flowers of pale periwinkle petals.
4. Elliptic to lanceolate foliage of silvery green.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
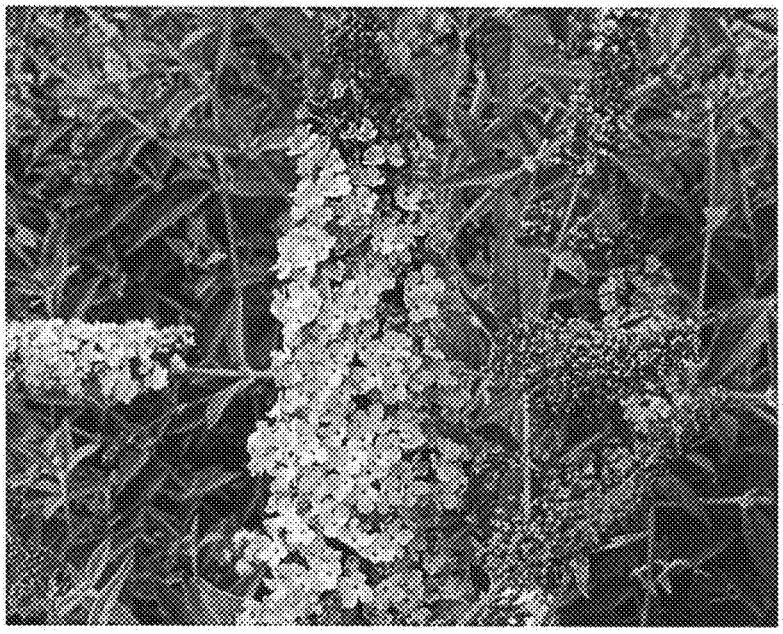
FIG. 1 shows a close-up of the flowers.
Figure 2:
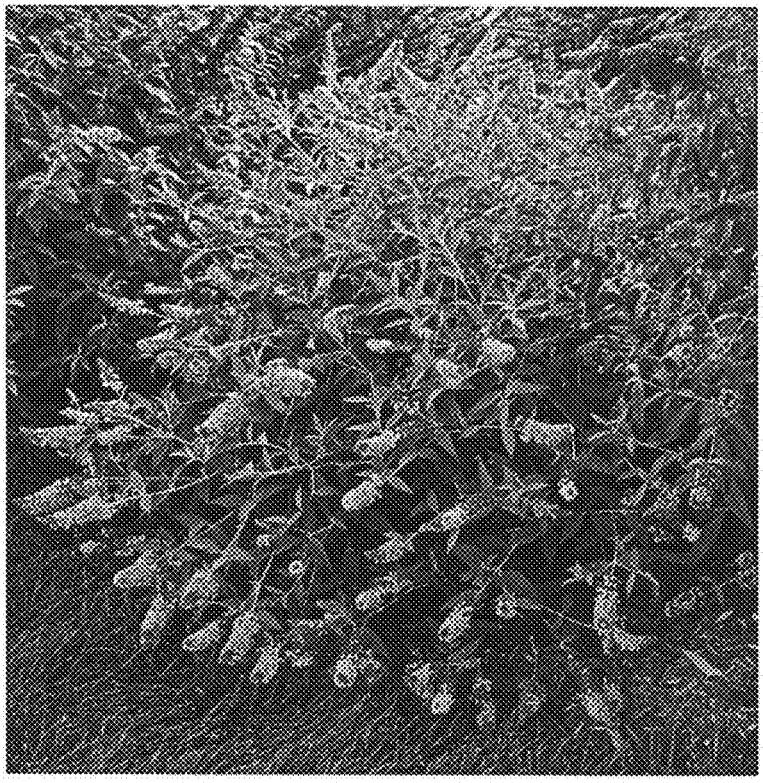
FIG. 2 shows the habit of a three-year-old plant in mid-season flowering.

The following descriptions and color references are based on the 2001 edition of The Royal Horticultural Society Colour Chart except where common dictionary terms are used. The new plant, *Buddleia* 'Glass Slippers', has not been observed under all possible environments. The phenotype may vary slightly with different environmental conditions, such as temperature, light, fertility, moisture and maturity levels, but without any change in the genotype. The following observations and size descriptions are of three-year-old plants in the loamy-sand, full-sun, field trials at a nursery in Zeeland, Mich. with supplemental fertilizer and water as needed. The plants are natural habit and were not treated with plant growth regulators, nor were they pinched at any time in the growth year except to cut back woody stems to about 15 cm tall in fall or early spring to promote new growth and flowering.

Parentage: Proprietary hybrid #HK10-212-01 (not patented) as the female or pod parent times an unknown open-pollination as the male or pollen parent.

Propagation:

*Method*.—Softwood cuttings.

*Time to initiate roots*.—About two weeks.

*Rooting habit*.—Normal, dense and thick at base to about 1.5 cm diameter; fibrous, branching.

*Root color*.—Creamy white between RHS 159A and lighter than RHS 159 D depending on soil type; becoming woody to 1.5 cm diameter.

*Crop time*.—Under normal summer growing conditions 12 to 16 weeks to flower in a four-liter container from cutting. Plant vigor is very good.

Plant description:

*Plant shape and habit*.—Winter-hardy, herbaceous, semi-woody, well-branched shrub with about 14 thick upright and branched main stems producing an upright mound about 135 cm tall and about 150 cm wide.

*Stem*.—Rounded and woody in lower portion rounded in cross section with exfoliating bark; younger upper portion puberulent and quadrangular in cross section; strong and flexible; average about 41 cm tall from soil line to just below first flower branches, and about 1.2 cm diameter at the base; before distal flowers about 13 branches per main stem extending at about 35° to 45° angle from horizontal.

*Stem color*.—Just below expanding leaves lighter than RHS 192D and RHS 196C with slight tinting of nearest RHS 176B, midway up stem nearest RHS 145D with tinting of nearest RHS 176B and striated in about basal 12 cm with fissures of nearest RHS 165D and between RHS 165A and RHS 165B.

*Plant size*.—Unpinched plant with stems flowering to about 135 cm tall; overall plant about 150 cm wide.

*Internode*.—About 15 nodes per stem, average internode length about 7.0 cm on unpinched plant; upper nodes more pubescent than lower nodes.

*Node color*.—Same color as surrounding stem to slightly more tinted with RHS 178B.

Foliage description: Opposite, decussate; serrulate; puberulent abaxial and adaxial becoming more glabrous on adaxial surface as the leaves age; elliptic to lanceolate with attenuate base and acute to narrowly acute apex; no foliar fragrance detected.

*Leaf blade size*.—To about 14.0 cm long and about 5.0 cm wide, average about 13.0 cm long and about 4.5 cm wide; becoming smaller in distal portion of stem.

*Foliage color*.—Young expanding leaf adaxial side nearest RHS 138B and abaxial lighter than RHS 192D and RHS 196C; mature leaves adaxial side between RHS 139A and RHS 137A and abaxial and lighter than RHS 193D.

*Veins*.—Reticulate; abaxial raised, adaxial slightly impressed, puberulent abaxial and adaxial becoming glabrous adaxial.

*Vein color*.—Young expanding adaxial and abaxial same color as surrounding leaf; mature leaf adaxial main vein nearest RHS 145C and lateral veins same color as surround leaf, abaxial main vein nearest RHS N144A and lateral veins between RHS 145A and RHS 145B.

*Petioles*.—Glaucous and glabrous adaxial, pubescent abaxial; flatted partially top to bottom; average about 1.0 cm long and about 2.0 mm wide at the point of attachment to stem.

*Petiole color*.—Adaxial margins nearest RHS 139B and center vein nearest between RHS 147D and RHS 145C, abaxial nearest RHS 145D.

Inflorescence description: Glomerate thyrse consisting of about 600 self-cleaning, tightly-congested, salverform flowers; to about 33.5 cm long and 7.0 cm wide; beginning in mid-July and continuing until late October in Michigan.

*Buds*.—Narrowly spatulate, apex rounded; one day prior to opening about 8.0 mm long and about 3.0 mm in diameter in club, tube portion about 1.0 mm diameter and about 6.0 mm long.

*Bud color*.—Nearest RHS 85A in club portion, and tube nearest RHS N77B; buds about three days from opening nearest RHS 77B in the club and nearest RHS N82B in the tube.

*Sepals*.—Typically four, proximal two-thirds connate adpressed to corolla tube; acute apex; glabrous adaxial and pubescent abaxial; margin entire, edentate; fused in about the basal 1.5 mm and split in about the terminal 1.0 mm; forming a corolla about 4.0 mm long and about 1.5 mm across; individually less than about 1.0 mm wide at point of fusion.

*Sepal color*.—Adaxial nearest RHS 144D, abaxial between RHS 144A and RHS 144B; abaxial between RHS N77A and RHS N79A in regions of intense light exposure.

*Flowers fragrance*.—Pleasantly and distinctly sweet.

*Petals*.—Four; glabrous; fused into salverform with typically straight cylindrical tube about 7.0 mm long and 1.5 mm diameter, and a flattened face about 7.0 mm across; petal blade rounded with crenate margin; blade to about 2.5 mm across and about 3.0 mm long from fused face; center flattened face portion of blade fused about 1.5 mm.

*Petal color*.—Adaxial center between RHS 28B and RHS N25A in the tube, fading or lightening to just before the face of a thin irregular band of less than 0.5 mm width of between RHS 17B and RHS 17C, adaxial face blades between RHS 85A and RHS 92C; abaxial tube between RHS 53A and RHS 53B and abaxial petal blades nearest RHS 85A.

*Gynoecium*.—Pistil: one; about 3.5 mm long; Style: short, round, glabrous; about 1.5 mm long and less than 0.2 mm diameter; color nearest RHS 144D; Stigma: oblong, minutely puberulent; about 1.0 mm in long and about 0.7 mm diameter; color nearest RHS 143B; Ovary: superior; globose; about 1.0 mm across at base and 1.0 mm tall; distally tapering to style; color between RHS 144C and RHS 144D.

*Androecium*.—Not observed in any flowers examined; Anthers: not observed; Pollen: not observed.

*Pedicel*.—Short, puberulent; about 2.0 mm long and about 0.5 mm diameter; color between RHS 144A and RHS 138B with dark speckling of nearest RHS N187A.

*Peduncle*.—Quadrangular, pubescent, flexible and strong; to about 33.5 cm long and about 3.5 mm across just below flowers.

*Peduncle color*.—Between RHS 148D and RHS 148C.

*Fruit*.—Moderate fruit set; oblong with acute apex; glabrous, bi-valved, septicidal capsule; about 8.0 mm long and about 3.0 mm diameter.

*Fruit color*.—As maturing between RHS 187B and RHS 187C; when mature and dehiscing between RHS 177B and RHS 177C.

*Seed*.—Elongated ellipse with sharply acute ends; less than about 2.0 mm long and about 0.1 mm diameter in center.

*Seed color*.—Nearest RHS 200A.

Disease resistance: Resistance to deer browsing has been observed. Further resistance beyond that of other known winter-hardy butterfly bush cultivars has not been noted. The plant grows best with plenty of moisture and adequate drainage, but is able to tolerate some drought when mature. Hardiness at least from USDA zone 6 through 10.

I claim:

1. A new cultivar of winter-hardy butterfly bush *Buddleia* plant named 'Glass Slippers' as herein illustrated and described, suitable for potted plant culture, landscaping as a specimen or en masse or for cut flower purposes.

* * * * *